(12) United States Patent
Jakubowicz

(10) Patent No.: US 11,680,945 B2
(45) Date of Patent: Jun. 20, 2023

(54) ASSAY DEVICE HAVING A WASH PORT

(71) Applicant: Ortho-Clinical Diagnostics, Inc., Raritan, NJ (US)

(72) Inventor: Raymond F. Jakubowicz, Rush, NY (US)

(73) Assignee: Ortho Clinical Diagnostics, Inc., Raritan, NJ (US)

(*) Notice: Subject to any disclaimer, the term of this patent is extended or adjusted under 35 U.S.C. 154(b) by 361 days.

(21) Appl. No.: 17/120,798

(22) Filed: Dec. 14, 2020

(65) Prior Publication Data
US 2021/0140960 A1 May 13, 2021

Related U.S. Application Data

(62) Division of application No. 15/102,131, filed as application No. PCT/US2014/068808 on Dec. 5, 2014, now Pat. No. 10,877,031.

(60) Provisional application No. 61/912,673, filed on Dec. 6, 2013.

(51) Int. Cl.
*B01L 3/00* (2006.01)
*G01N 33/558* (2006.01)

(52) U.S. Cl.
CPC ......... *G01N 33/558* (2013.01); *B01L 3/5023* (2013.01); *B01L 2200/141* (2013.01); *B01L 2200/142* (2013.01); *B01L 2300/069* (2013.01); *B01L 2300/0627* (2013.01); *B01L 2400/0406* (2013.01)

(58) Field of Classification Search
None
See application file for complete search history.

(56) References Cited

U.S. PATENT DOCUMENTS

2012/0058465 A1* 3/2012 Mori ................ G01N 33/54386
435/5

* cited by examiner

*Primary Examiner* — Rebecca M Giere
(74) *Attorney, Agent, or Firm* — K&L Gates LLP; Luis C. Cullman; Dennis A. Majewski

(57) ABSTRACT

A test element for an assay includes: a cartridge having a housing which includes a priming pad capable of containing a liquid fluid, a wash port having an opening in the housing, and an opening for directly or indirectly applying a sample; and an assay device positioned within the cartridge in fluid communication with the wash port containing an analytical reagent.

10 Claims, 5 Drawing Sheets

ASSAY DEVICE HAVING A WASH PORT

CROSS REFERENCE TO RELATED APPLICATIONS

This patent application is a divisional of U.S. Ser. No. 15/102,131, filed Jun. 6, 2016, which claims priority to Patent Cooperation Treaty (PCT) Application Number PCT/US2014/68808 filed Dec. 5, 2014, which claims priority to U.S. Provisional Application No. 61/912,673, filed Dec. 6, 2013, the disclosure of each noted document being incorporated by reference in its entirety.

FIELD OF THE INVENTION

The present invention relates to the field of diagnostic assays, and in particular to lateral flow assays where an analyte to be detected is present in a biological or non-biological sample. The present invention further relates to wash systems for diagnostic assays.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture. Understandably it is difficult to meet all these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

Another type of assay device is a non-porous assay having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

The assay devices described in the above publications typically include at least one sample addition zone, a reagent zone, at least one detection zone, and at least one wicking zone. The zones form a flow path by which sample flows from the sample addition zone to the wicking zone. Also included are capture elements, such as antibodies, in the detection zone, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay). Unbound dissolved conjugate material will be swept past the detection zone into the at least one wicking zone.

An instrument or reader such as that disclosed US Patent Publication Nos. US 20060289787A1 and US 20070231883A1, and U.S. Pat. Nos. 7,416,700 and 6,139,800, all of which are incorporated herein by reference in their entireties, is able to detect the bound conjugated material in the detection zone. Common labels include fluorescent dyes that can be detected by instruments which excite the fluorescent dyes and incorporate a detector capable of detecting the fluorescent dyes.

The sample size for such typical assay devices are generally on the order of 200 µl. Such a sample size requires a venous blood draw from a medical professional such as a phlebotomist. There is an increasing need for lateral flow devices that are able to function with a much smaller sample size to accommodate the amount of blood available from a so-called "finger stick" blood draw, which is on the order of 25 µl or less. Such a small amount of sample is the amount of blood in a drop of blood after pricking a fingertip with a lancet. Home blood glucose meters typically use a drop of blood obtained in such a fashion to provide glucose levels in blood. Such a smaller sample size would not require a medical professional to draw the blood and would provide greater comfort to the patients providing the sample for analysis.

For some assays, particularly immunoassays, it is important that unbound signal producing reagents be removed from bound signal producing reagents before the detection zone is read by an instrument, such as a fluorometer. In lateral flow assays, such as those described above, the flowing sample itself, is often used as the wash fluid to remove unbound from bound signal generating reagent from the detection zone. However, in those systems that are being designed to use less sample volume, use of the sample as the wash, after conjugate dissolution, becomes less of an option. In those reduced volume systems, it becomes desirable to employ a wash reagent. The addition of a wash fluid to completely remove unbound reactants from the reaction zone is a desired feature in such low sample volume lateral flow assays. In order to achieve required sensitivity or specificity it may also be necessary to remove unbound materials associated with the sample itself that may provide non-specific signal. Wash fluids are typically dispensed using a metering system that operates over a duration of useful life which can be single use, a day or as long as 3 months. Depending on utilization rate, long periods of idle time can create issues with wash systems caused by evaporation and dry out of probes, buildup of solid materials on probes and surrounding surfaces. These issues are described in more detail below.

Immunoassay wash systems are typically composed of 1) liquid reservoirs for long term storage of wash reagents 2) mechanical pumps for aspiration and dispensing of wash reagents under computer control and 3) dispensing probes enabling precise physical positioning for wash reagent dispense. Wash reagent compositions may contain salts, proteins, surfactants, displacers and other solids (A typical formulation might include Phosphate Buffered Saline, BSA, TX-100, and ProClin 950). This composition can be problematic for long term onboard storage where infrequent utilization provides little opportunity for rewetting and purging of dispense probes, as may be the case for point of care devices in which storage of wash reagent for periods of 3 months are desired. These wash systems are prone to fluid evaporation which can cause dispense probe tip dry out, leading to tip plugging of metering probe orifices caused by the residual buildup of wash solids after evaporation. Wash solutions may become concentrated at the probe and provide significant concentration gradients from wash to wash. Another issue is that a common wash is typically formulated that has to perform for all assays and may not be optimal for an individual assay. Opportunities also exist to use reagents other than wash reagents to enhance signal output or create other immuno reactions downstream of the wash zone. Still another issue is that a wash fluid formulation is not stable for long periods of time and there is required separation of some of the wash fluid components from others.

SUMMARY OF THE INVENTION

The present invention is directed to an assay device that alleviates one or more the foregoing problems described above.

One aspect of the invention is directed to a test element for an assay. The test element includes: a cartridge having a housing including a priming pad capable of containing a liquid fluid; a wash port having an opening in the housing; and an opening for directly or indirectly applying a sample. The test element further includes an assay device positioned within the cartridge in fluid communication with the wash port containing an analytical reagent. In a preferred embodiment, the assay device is a lateral flow assay device.

Another aspect of the invention is directed to a point-of-care system. The point-of-care system includes a test element having: a cartridge having a housing which includes a priming pad capable of containing a liquid fluid; a wash port having an opening in the housing; and an opening for directly or indirectly applying a sample; and a sample manipulation portion positioned within the cartridge in fluid communication with the wash port and having an assay device containing an analytical reagent. The point-of-care system further includes: a measurement system having a housing having a port into which the test element is inserted, an optical energy source, and an optical energy detector configured to detect a detectable signal from the analytical reagent; a wash probe for dispensing a liquid fluid onto the wash port; and a source of liquid fluid.

Still another aspect of the invention is directed to a method for adding a wash fluid to an assay. The method includes: providing a test element for an assay including a cartridge having a housing which includes a priming pad capable of containing a liquid fluid, a wash port having an opening in the housing, and an opening for directly or indirectly applying a sample, and an assay device positioned within the cartridge in fluid communication with the wash port containing an analytical reagent; providing a wash probe; providing a source of liquid fluid; positioning the wash probe over the priming pad; dispensing a quantity of liquid fluid onto the priming pad; positioning the wash probe over the wash port; and dispensing a selected amount of liquid fluid into the wash port.

Yet another aspect of the invention is directed to a method of performing an assay on a liquid sample for the detection of one or more analyte(s) of interest. The method includes providing a test element for an assay. The test element includes: a cartridge having a housing which includes a priming pad capable of containing water; a wash port having a material capable of supporting capillary flow; and an opening for directly or indirectly applying a sample; and a sample manipulation portion positioned within the cartridge in fluid communication with the wash port and having a lateral flow assay device which includes a liquid sample zone, a reagent zone downstream and in fluid communication with the sample addition zone containing a reagent material, a detection zone in fluid communication with the reagent zone, and a wicking zone in fluid communication with the detection zone having a capacity to receive liquid sample flowing from the detection zone, wherein the sample receiving zone, the reagent zone, the detection zone and the wicking zone define a fluid flow path and at least a part of the fluid flow path has a substrate. The method further includes: depositing a liquid sample containing the analyte(s) of interest onto the sample zone; moving the sample by capillary action into the reagent zone where it dissolves the reagent material; flowing the sample away from the reagent zone having a dissolved reagent plume and into a detection zone by capillary action, where the analyte(s) are detected by reading a signal that is generated to determine the presence or concentration of the analyte(s); flowing the sample and any other unbound material into the wicking zone, wherein the method further includes providing a wash probe; providing a source of a liquid fluid; positioning the wash probe over the priming pad; dispensing a quantity of the liquid fluid onto the priming pad; positioning the wash probe over the wash port; dispensing a selected amount of the liquid fluid into the wash port.

Further objects, features and advantages of the present invention will be apparent to those skilled in the art from detailed consideration of the preferred embodiments that follow.

DETAILED DESCRIPTION OF PREFERRED EMBODIMENTS

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be acted upon by a sample manipulation device. In a preferred embodiment, the sample is subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

Non-biological samples can be aqueous or non-aqueous, for example waste water samples for environmental testing and solutions having organic solvents, such as alcohols for chemical processing. One aspect of the invention is directed to a sample collection device for collecting a sample, such as a blood or blood-based sample, and delivering it to a sample manipulation device that overcomes at least some of the disadvantages of known sample collection devices.

One aspect of the present invention provides a test element that can be part of a liquid wash system that includes a pure water reservoir with no added solids allowing storage for extended periods of time without plugging. It also provides for solids to be rehydrated for use, as part of the test element and allows for single use purging and priming of the wash system in an absorbent area (i.e., priming pad) contained within the consumable shell (i.e., cartridge) and is disposed with the removal of the test element at the completion of the test. No internal cleaning is required. Another aspect of the invention provides a test element that can be part of a liquid wash system that includes a pre-mixed wash solution reservoir along with the priming pad. In another aspect, the present invention provides a liquid wash system that includes a liquid wash fluid that combines with solids to be dissolved when exposed to the liquid wash fluid to form a complete wash fluid formulation.

Figure 1:
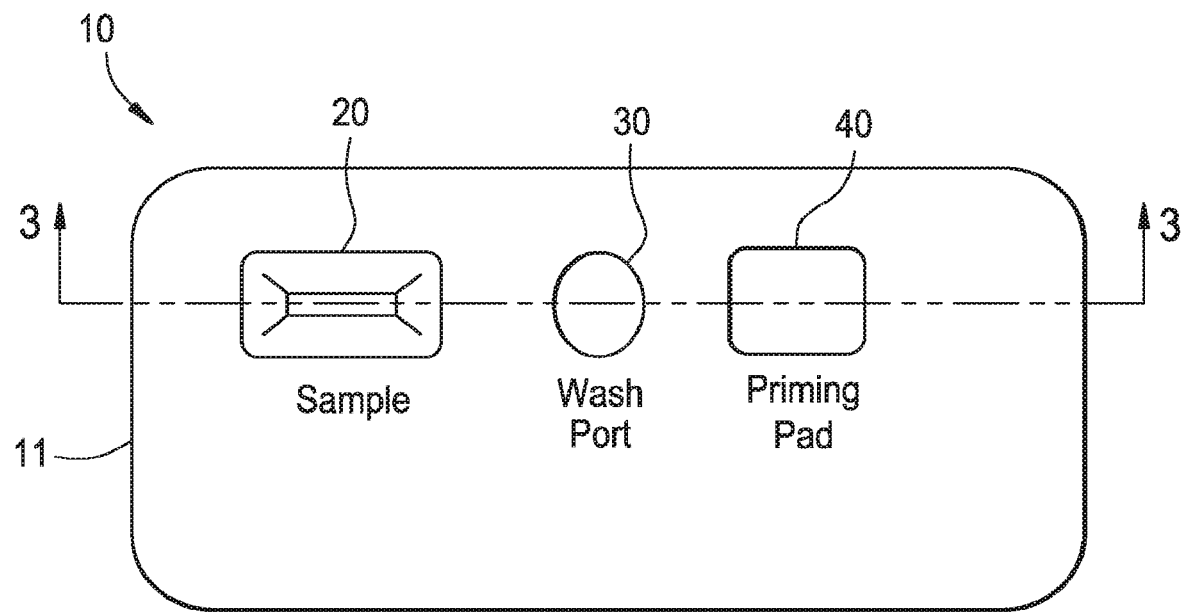
FIG. 1 shows a top view of a test element according a preferred embodiment of the present invention.
Figure 2:
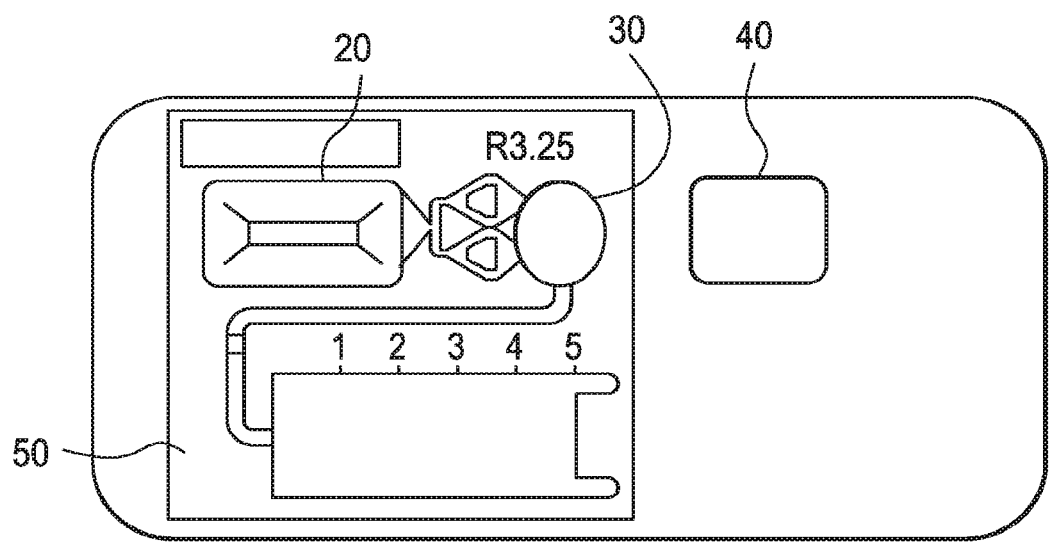
FIG. 2 shows a cutaway view of a test element according to one embodiment of the invention.

FIG. 1 shows a top view of a test element 10 having a housing 11 according to one preferred embodiment. The test element includes a sample addition opening 20, a wash port 30 and a priming pad 40. The positions of these features of the test element relative to the assay device 50 are shown in the cutaway view in FIG. 2. Additional features of the assay device are described below.

Figure 3:
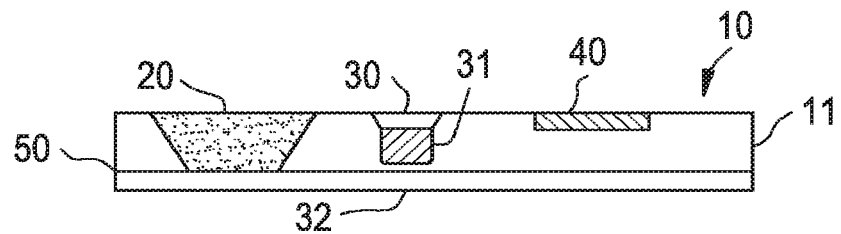
FIG. 3 shows a cross-sectional view along lines 3-3 of FIG. 1.

FIG. 3 shows a cutaway view of FIG. 1 along lines 3-3. In this embodiment, the sample addition opening 20, allows sample to be directly applied to the assay device. In the case of whole blood, a filter may be provided to separate the red blood cells from the plasma before the assay device 40. Sample may also be applied indirectly, such as through a removable sample collection device as described in application Ser. No. 61/790,961, entitled DISK-SHAPED CAPILLARY SAMPLE COLLECTION DEVICE and Ser. No. 61/791,334 entitled ROTATABLE FLUID SAMPLE COLLEC HON DEVICE both filed on Mar. 15, 2013 and both incorporated herein by reference in their entireties.

The priming pad 40 is capable of holding a liquid fluid such as water or a wash fluid, such as described above. The priming pad preferably contains a bibulous or absorbent material that absorbs the liquid fluid, such as nitrocellulose, cotton fibers, paper (e.g., Whatman.RTM. 3 mm paper, and Filtrona.RTM. products), synthetic polymeric materials (e.g., nitrocellulose, nylon), plastics and plastic spheres (e.g., Porex.RTM. plastic beads; materials used in fabricating ballpoint pens), such as those made from polypropylene, polyethylene, polyvinylidene fluoride, ethylene vinylacetate, acrylonitrile, and polytetrafluoroethylene. Other non-limiting examples include nanoparticles/spheres/tubes.

Any absorbable material may be used as long as it is capable of retaining the liquid wash fluid in an amount sufficient to purge the liquid fluid dispensing probe described in more detail below.

The wash port 30 is an opening in the cartridge housing 11 for applying the liquid fluid such as from a dispensing probe. The wash port can be simply an opening in the cartridge 11, or may have sidewalls 31 extending in the direction toward the assay device, such as the assay device to form a column that can contain the optional filter material. In a preferred embodiment, the wash port includes a material capable of supporting capillary flow 32, such as a filter material. The filter material can be impregnated with various wash materials, reagents, surfactants and can be coated with hydrophilic coatings to enhance flow in the filter. Examples of materials can include anti-hemolytic agents such as amino acids (e.g., glycine or histidine), non-hemolytic, non-ionic surfactant, buffers, such as citrate, etc. The wash port filter material can be coated in place (i.e., already in the wash port) on the top surface using ink jet or similar processes. Alternatively, the filter can be coated in bulk during the manufacturing process of the test element and inserted into the wash port as needed. In another embodiment the wash port may be simply a structure with no filter but coating on the walls of the formed column walls. The column walls may contain features for supporting the coated materials. In still another embodiment, some or all of the coating materials may be coated on the assay device itself.

If no wash is required for a given assay, or if the liquid fluid being dispensed by the dispensing probe is a pre-made wash fluid described more fully below, the filter is not inserted and the wash port is left blank.

In another embodiment, the test element may contain two or more wash ports. For example, in the instance of an assay device, one wash port could be positioned between the reagent zone and detection zone to assist in removing unbound reagents from the detection zone, whereas the other wash port could be positioned before the sample zone to assist in pushing sample from the sample zone and into the rest of the assay device. In another embodiment, the other wash port could be positioned immediately after the sample zone to stop the flow of sample if desired.

In a preferred embodiment, the capacity of the wash port can contain the full desired dispense volume, or the wash system can apply fluid discretely over some time interval. The typical flow rate of the flow path of the assay device is approximately 1.0 µL per minute. The flow path controls the take up of wash fluid from the wash port at this rate allowing sufficient time for solids (dried and stored in the wash port, such as on the filter) to dissolve into the liquid wash and into the flow channel. The wash liquid is forced into contact with the flow path by gravity and from the pressure of fluid head in the wash port column.

Figure 4:
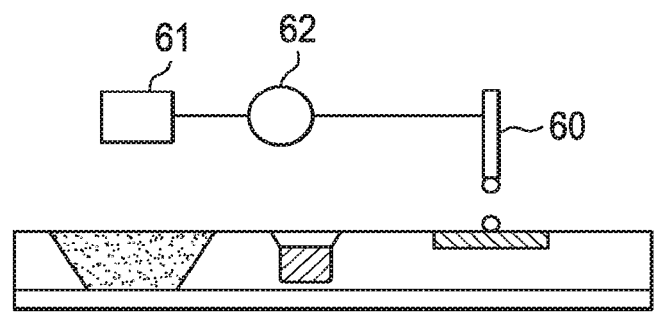
FIG. 4 shows the view of FIG. 3 along with a dispensing probe according to one embodiment of the invention.
Figure 5:
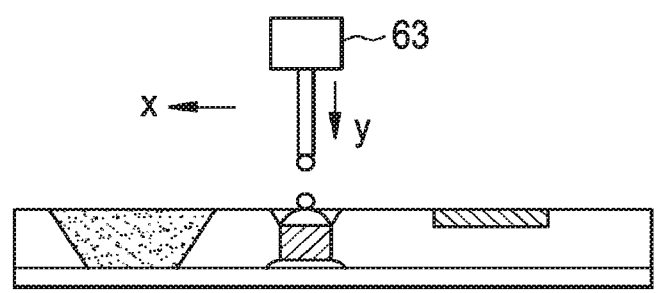
FIG. 5 shows the view of FIG. 3 along with a dispensing probe according to one embodiment of the invention.

According to another aspect of the invention a dispensing probe for dispensing a liquid fluid onto the wash port is also provided. A schematic dispensing probe 60 is shown in FIGS. 4 and 5. Dispensing probes for dispensing fluids, such as sample or wash fluids, are generally well known in the art as described in U.S. Pat. Nos. 6,484,556, 5,133,392, 4,794,085, 5,142,849 and 5,665,601, all incorporated herein by reference in their entireties. The dispensing probe includes a source of liquid fluid 61, such as a reservoir chamber, and a pump 62, such as a rotary piston pump. The probe can also include a probe drive system 63 for moving the probe in an x and y direction as shown in FIG. 5. This allows the probe to be moved from the priming pad 40 to the wash port 30 and any other positioned required. Alternatively, the probe can be stationary and the test element can be moved to position the wash port and priming pad under the probe.

Figure 6:
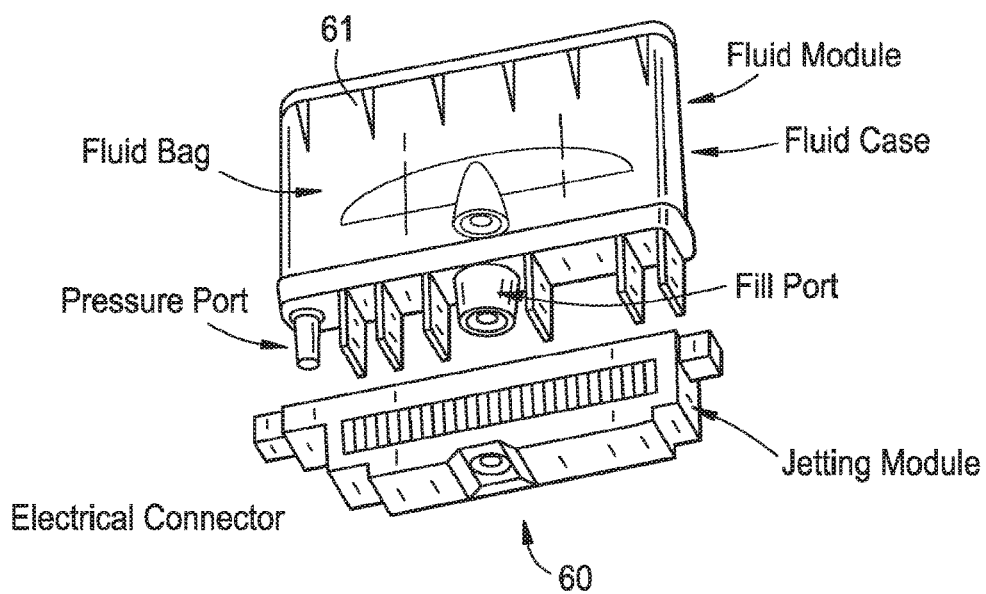
FIG. 6 shows an ink jet dispensing probe according to one embodiment of the invention.

As noted above, the source of liquid fluid can be either water, or a pre-mixed wash fluid. In the case of a pre-mixed reagent, a particularly useful dispensing probe is in the form of an ink jet printer can be used. In this embodiment, separate ink jet cartridges containing different wash fluids for different assays can be interchangeably used with a common print head, i.e., dispensing probe, depending on the assay being performed. A preferred ink-jet type configuration is shown in FIG. 6. As shown in FIG. 6, a detachable reservoir chamber 61 can be used with ink jet nozzle 60.

The test element also includes an assay device. These assays are frequently expected to give a fast and reliable result, while being easy to use and inexpensive to manufacture.

Examples of diagnostic assays include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

Figure 7:
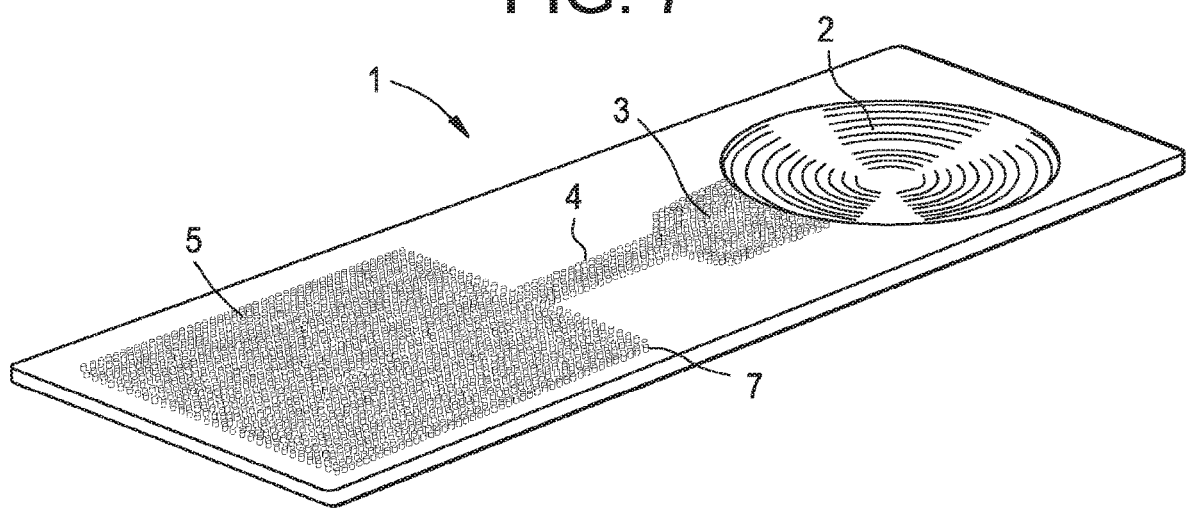
FIG. 7 shows an embodiment of an assay device usable in the present invention.

A non-porous assay device 50 is shown in FIG. 7. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into die detection zone, the conjugated material will be captured by the capture elements such as via complex of conjugated material and analyte (as in a "sandwich" assay) or directly (as in a "competitive" assay. Unbound dissolved conjugate material will be swept past the detection zone into the at least one wicking zone 5.

Figure 8:
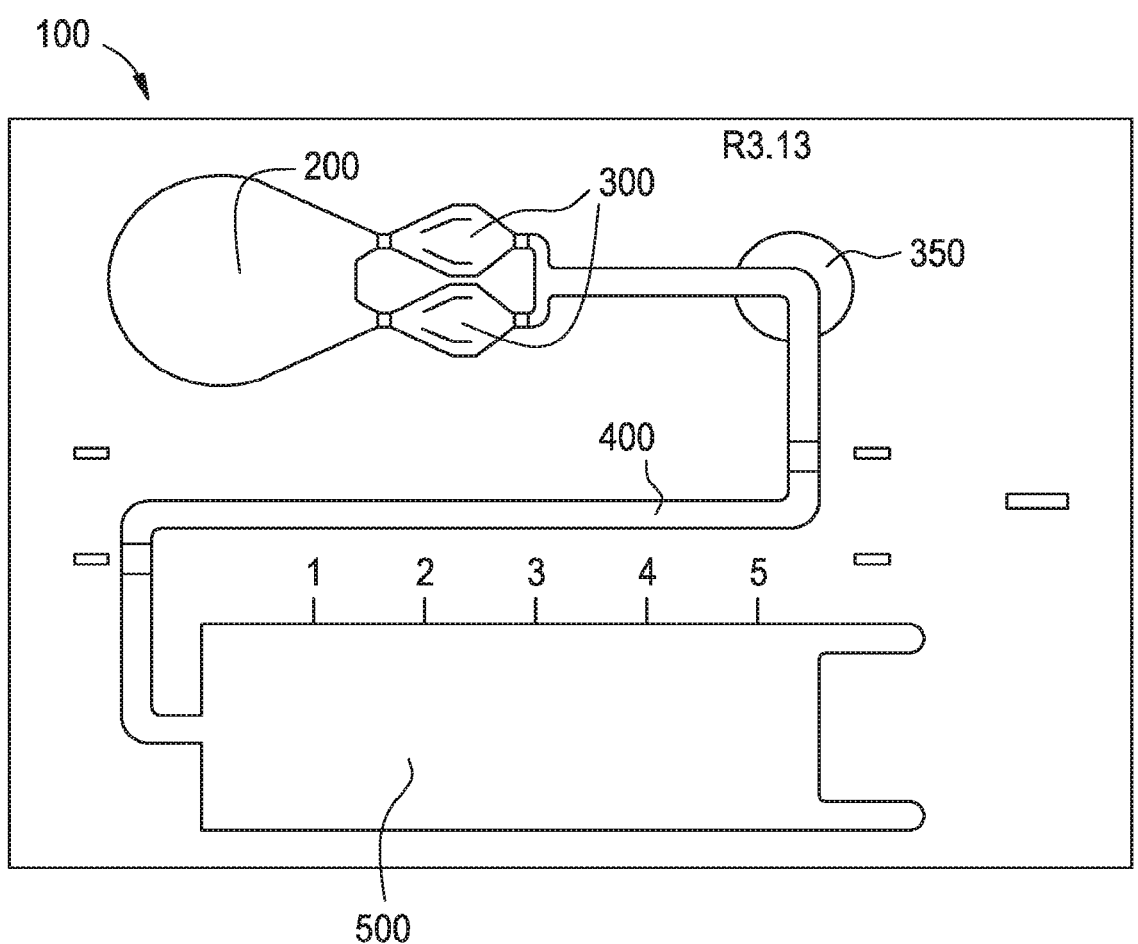
FIG. 8 shows an embodiment of an assay device according to one embodiment of the present invention.

FIG. 8 shows a schematic view of another preferred lateral flow assay device 50. The assay device 100 has at least one sample zone (also referred to as sample addition zone) 200, at least one reagent zone 300, at least one detection zone 400, and at least one wicking zone 500. The zones form a flow path by which sample flows from the sample addition zone to the wicking zone.

Components of the assay device and any other part of the working element (i.e., a physical structure of the device whether or not a discrete piece from other parts of the device) can be prepared from copolymers, blends, laminates, metalized foils, metalized films or metals. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalk do not contribute to the capillary action of the liquid, then a gap can be provided between the outermost projections and the sidewalls to keep the liquid contained in the flow path defined by the projections. FIG. 7 shows projections 7.

In one embodiment the flow path is at least partially open. In another embodiment the flow path is entirely open. Open means that there is no lid or cover at a capillary distance. Thus the cover, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably 40 to about 100 µm, and a gap or gaps between the projections of about 3 to about 200 µm, preferably 5 to about 50 µm or 10 to 50 µm from each other. The flow channel may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone 200, also referred to as the liquid sample addition zone, receives sample directly or indirectly. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 7. In those devices that can use finger stick volumes of blood, the sample can be directly touched off from the finger, or by a capillary pipette.

Located between the sample addition zone and the detection zone is a reagent zone 300. The reagent zone can include reagent material(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. In one preferred embodiment, the reagent zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}$I and $^{32}$P.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in a "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 350 in FIG. 8. The reagent addition zone can allow addition of a reagent externally from the device. For example, the reagent addition zone may be used to add an interrupting reagent that may be used to wash the sample and other unbound components present in the fluid flow path into the wicking zone. In a preferred embodiment the reagent addition zone 350 is located after the reagent zone 300.

Downstream from the liquid sample zone and the reagent zone is the detection zone 400 which is in fluid communication with the sample addition zone. The detection zone 400 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above are significantly narrower, e.g., 1.5 mm or less, preferably 0.5 to 1.2 mm.

The detection zone is where any detectable signal is read. In a preferred embodiment attached to the projections in the detection zone are capture elements. The capture elements can include binding partners for the conjugate or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the detection zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the detection zone or those added through the reagent addition zone. The reagent in the sample flowing from the reagent zone, but before the reagent addition zone is considered to be a reagent plume. The reagent plume can include the conjugate having both the detection element and binding partner, in which case it is often referred to as a conjugate plume. It is at the detection zone where a wash process is typically required.

Downstream from the detection zone is a wicking zone 500 in fluid communication with the detection zone. The wicking zone is an area of the assay device with the capacity of receiving liquid sample and any other material in the flow path, e.g., unbound reagents, wash fluids, etc. The wicking zone provides a capillary force to continue moving the liquid sample through and out of the detection zone. The wicking zone can include a porous material such as nitrocellulose or can be a non-porous structure such as the projections described herein. The wicking zone can also include non-capillary fluid driving means, such as using evaporative heating or a pump. Further details of wicking zones as used in assay devices according to the present invention can be found in patent publications US 2005/0042766 and US 2006/0239859, both of which are incorporated herein by reference in their entireties. Wicking zones are also described in copending patent application entitled "Controlling Fluid Flow Through An Assay Device," Ser. No. 13/744,641, filed on Jan. 18, 2013, and incorporated by reference in its entirety.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

The assay device of the present invention can be used with a device for reading (a reader or measurement device) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

Another aspect of the invention includes a point-of-care (POC) system for performing diagnostic assays. A POC system is a system that includes a reader that is desktop size or smaller and is typically used in a doctor's office or emergency room of a hospital. The POC system includes the test element described above containing the cartridge having the priming pad, wash port and opening for applying a sample and assay device positioned within the cartridge.

Figure 9B:
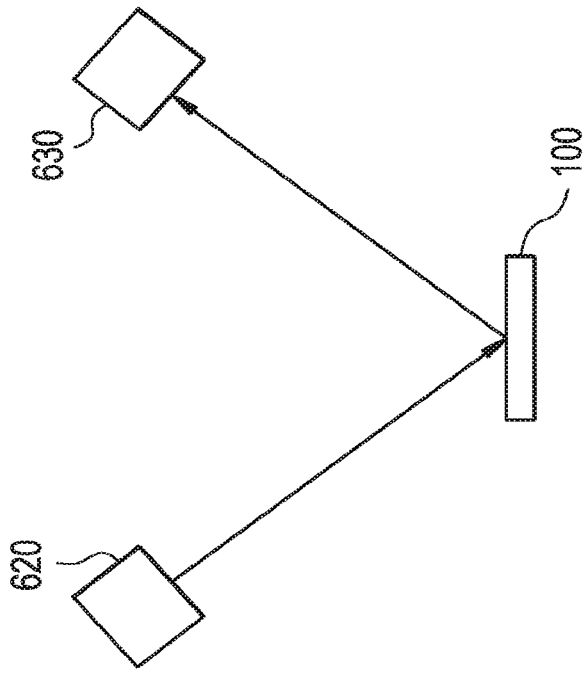
FIGS. 9A and 9B show a schematic depiction of a reader usable in the present invention, along with its measurement optics according to one embodiment of the present invention.
Figure 9A:
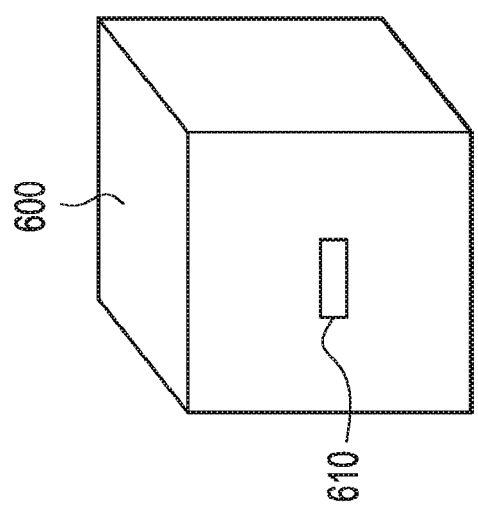

In addition, the POC system includes a measurement system. Such a measurement system or reader 600 as shown schematically in FIG. 9A and includes a housing having a port 610 that accepts the test element either before or after sample has been added. An optical energy source 620 is provided, such as a laser diode or LED, capable of directing energy, such as visible light to the analytical reagent on the test element as shown schematically in FIG. 9B. The measurement system also includes a detector 630 that is configured to detect a detectable signal from the assay device 100.

Also part of the POC system is the liquid fluid dispensing probe and a source of liquid fluid as shown in connection with FIGS. 3-5. Preferably, the dispensing probe is an integral part of the measurement system and is controlled by the microprocessor that controls the other aspects of the system as is well known in the art.

Another aspect of the invention is directed to a method of washing an assay that includes providing the test element and probe system described above. The dispensing probe is positioned over the priming pad. The probe then dispenses a sufficient amount of liquid fluid onto the priming pad, in an amount sufficient to adequately prime the probe. The advantages of dispensing into the probe first is twofold. First, there may be dried residue on the probe that results from the probe at least partially drying out between uses, particularly if there is a sufficient time between dispenses. By first priming the probe, the dried residue will be dissolved and dispensed into the priming pad and will not affect the assay results. Second, partial drying of the probe may result in an incorrect dispense volume. For example, if a probe has an internal volume of 10 ul and if it has completely dried out such that no fluid remains, and if the dispense volume for the wash is 10 ul, then when the pump attempts to dispense the 10 ul, none will be dispensed into the wash port because all 10 ul is used to refill the probe. By priming the probe, the probe is "reset" so that the intended dispense volume can be delivered to the assay device.

The priming pad, preferably containing an absorbent material as described above is capable of retaining the dispensed liquid fluid, and will hold the fluid without spillage even as the test element is removed from the measurement system and subsequently disposed of. After priming the probe is then moved in a position over the wash port where a pre-selected amount of the liquid fluid is dispensed into the wash port and onto the assay device.

The invention also includes a method for performing an assay on a liquid sample for the detection of one or more analyte(s) of interest. A liquid sample containing the analyte(s) of interest is applied to the test element to begin test processing. The test element is then inserted into the measurement system that contains the detection elements and the wash system described above. Alternatively, the sample can also be applied to the test element after the test element has been inserted into the measurement system. The sample is dispensed on the sample zone of the assay device. If the sample is whole blood, the whole blood may first be filtered by the sample filter thus separating the red blood cells from the plasma and providing a source of plasma to assay device. However, in some embodiments, it may be possible to use whole blood in the assay, obviating the need for a separate filter.

The sample moves by capillary action into the reagent zone where it encounters reagent materials, e.g., labeled conjugate. The sample flows past the reagent material, dissolving the reagent material forming a reagent plume.

Next the sample and reagent plume move by capillary action into the detection zone. There a signal representative of the presence or concentration of the analyte(s) or control is produced. In a preferred embodiment the sample or the one or more reagents having a detection element is captured in the detection zone, such as by antibodies on the surface of the detection zone and a signal representative of the presence or concentration of the analyte(s) or control(s) is produced.

The reader as described above is then used to read the signal that is produced by the detection element to determine the presence or concentration of the analyte(s). The sample moves from the detection zone and into the wicking zone. The reader may read the signal immediately or a short time after the sample has moved through the detection zone.

Also, one or more washes may follow the sample through the device to wash any unbound detection element away from the detection zone. In this instance, the sample flows under the wash port, preferably making no contact with the filter material in the wash port as described above. The assay protocol for the particular assay determines the completion of conjugate dissolution and prepares the wash system for adding liquid fluid to the wash port. The test element incorporates the priming pad that allows the wash system to prime itself prior to initiating the wash. The pad can contain a volume of liquid sufficient to purge the probe and establish baseline metering before every use. The pad allows the fluid dispensed during priming to be contained for the duration of the test after which it is ejected from the analyzer with the spent test element. Once the purge is complete and the need for the wash event is determined. The element and/or probe is positioned at the wash port where the wash system dispenses de-ionized water or a pre-mixed wash fluid into the wash port via the dispense probe. The volume is determined by each specific assay wash protocol, and can range from 1.0 to 10.0 µL. The capacity of the wash port can contain the full desired dispense volume or the wash system can apply fluid discretely over some time interval as described above.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

The invention claimed is:

1. A wash system for a diagnostic assay, comprising:
   a test element for an assay comprising:
      a cartridge having a housing including an outer surface, the housing comprising
      a priming pad open to the outer surface and capable of containing a liquid fluid;
      a wash port having an opening in the outer surface on a same side of the housing as the priming pad; and
      an opening for directly or indirectly applying a sample; and
      an assay device positioned within the cartridge in fluid communication with the wash port containing an analytical reagent; and
   a dispensing probe for dispensing a liquid fluid onto the wash port,
   wherein the priming pad is fluidically isolated from the wash port and the assay device and wherein the priming pad is capable of retaining the liquid fluid such that the liquid fluid will not affect an assay result of the sample applied at the opening of the cartridge.

2. A wash system as claimed in claim 1, wherein the liquid fluid is selected from the group consisting of water and a wash fluid.

3. A wash system as claimed in claim 1, wherein the dispensing probe is an inkjet print head.

4. A point-of-care system comprising:
   a test element comprising:
      a cartridge having a housing including an outer surface, the housing comprising a priming pad open to the outer surface and capable of containing a liquid fluid;

a wash port having an opening in the outer surface on a same side of the housing as the priming pad; and
an opening for directly or indirectly applying a sample; and
a sample manipulation portion positioned within the cartridge in fluid communication with the wash port and having an assay device in fluid communication with the wash port containing an analytical reagent,
wherein the priming pad is fluidically isolated from the wash port and the assay device and wherein the priming pad is capable of retaining the liquid fluid such that the liquid fluid will not affect an assay result of the sample applied at the opening of the cartridge; and
a measurement system comprising:
a housing having a port into which the test element is inserted;
an optical energy source; an optical energy detector configured to detect a detectable signal from the analytical reagent;
a wash probe for dispensing a liquid fluid onto the wash port; and a source of liquid fluid.

5. A point-of-care system as claimed in claim 4, wherein the liquid fluid is selected from the group consisting of water and a wash fluid.

6. A point-of-care system as claimed m claim 4, wherein the dispensing probe is an ink-jet print head.

7. A method for adding a wash fluid to an assay, comprising:
providing a test element for an assay comprising:
a cartridge having a housing including an outer surface, the housing comprising
a priming pad open to the outer surface and capable of containing a liquid fluid;
a wash port having an opening in the outer surface on a same side of the housing as the priming pad; and
an opening for directly or indirectly applying a sample; and
an assay device positioned within the cartridge in fluid communication with the wash port containing an analytical reagent,
wherein the priming pad is fluidically isolated from the wash port and the assay device and wherein the priming pad is capable of retaining the liquid fluid such that the liquid fluid will not affect an assay result of the sample applied at the opening of the cartridge;
providing a wash probe;
providing a source of liquid fluid;
positioning the wash probe over the priming pad;
dispensing a quantity of liquid fluid onto the priming pad;
positioning the wash probe over the wash port; and
dispensing a selected amount of liquid fluid into the wash port.

8. A method of performing an assay on a liquid sample for the detection of one or more analyte(s) of interest, comprising: providing a test element for an assay comprising:
a cartridge having a housing including an outer surface, the housing comprising
a priming pad open to the outer surface and capable of containing water;
a wash port having a material capable of supporting capillary flow and having an opening in the outer surface on a same side of the housing as the priming pad; and
an opening for directly or indirectly applying a sample;
and a sample manipulation portion positioned within the cartridge in fluid communication with the wash port and having a lateral flow assay device in fluid communication with the wash port,
wherein the priming pad is fluidically isolated from the wash port and the assay device and wherein the priming pad is capable of retaining the liquid fluid such that the liquid fluid will not affect an assay result of the sample applied at the opening of the cartridge,
the lateral flow assay device comprising:
a liquid sample zone;
a reagent zone downstream and in fluid communication with the sample addition zone containing a reagent material;
a detection zone in fluid communication with the reagent zone; and
a wicking zone in fluid communication with the detection zone having a capacity to receive liquid sample flowing from the detection zone, wherein the sample receiving zone, the reagent zone, the detection zone and the wicking zone define a fluid flow path and at least a part of the fluid flow path has a substrate;
depositing a liquid sample containing the analyte(s) of interest onto the sample zone;
moving the sample by capillary action into the reagent zone where it dissolves the reagent material;
flowing the sample away from the reagent zone having a dissolved reagent plume and into a detection zone by capillary action, where the analyte(s) are detected by reading a signal that is generated to determine the presence or concentration of the analyte(s);
flowing the sample and any other unbound material into the wicking zone, wherein the method further comprises providing a wash probe;
providing a source of a liquid fluid;
positioning the wash probe over the priming pad; dispensing a quantity of the liquid fluid onto the priming pad; positioning the wash probe over the wash port; and
dispensing a selected amount of the liquid fluid into the wash port.

9. A method as claimed in claim 8, wherein at least a part of the fluid flow path includes projections which extend substantially vertically from the substrate,
wherein the projections have a height, cross-section and a distance between one another that defines a space between the projections capable of generating capillary flow parallel to the substrate surface.

10. A method as claimed in claim 8, wherein at least a part of the fluid flow path has a substrate surface and a porous media capable of generating capillary flow parallel to the substrate surface.

* * * * *